United States Patent [19]

Goss

[11] 4,227,526
[45] Oct. 14, 1980

[54] MECHANISM FOR AURALLY INSTRUCTING A PATIENT AND METHOD

[75] Inventor: Jack Goss, Pinellas Park, Fla.

[73] Assignee: Extracorporeal Medical Systems, Inc., Pinellas Park, Fla.

[21] Appl. No.: 895,916

[22] Filed: Apr. 13, 1978

[51] Int. Cl.³ .............................................. A61M 5/00
[52] U.S. Cl. ..................... 128/214 E; 128/DIG. 13; 210/85; 340/519; 360/12; 360/61
[58] Field of Search ......................... 35/8 A, 9 A, 9 C; 128/2 D, 2.05 R, 2.06 R, 2.1 A, 214 R, 670, 672-673, 709, 214 E, DIG. 13; 210/85; 360/12, 78, 61; 346/33 ME; 340/500, 502, 504, 506, 517, 519, 54

[56] References Cited

U.S. PATENT DOCUMENTS

| | | | |
|---|---|---|---|
| 3,582,949 | 6/1971 | Forst | 340/521 |
| 3,609,227 | 9/1971 | Kuljian | 35/35 C X |
| 3,857,383 | 12/1974 | Sommerfeld et al. | 128/2 D |
| 3,911,487 | 10/1975 | Ladriere | 360/78 X |
| 3,934,226 | 1/1976 | Stone et al. | 35/9 A |
| 4,004,577 | 1/1977 | Sarnoff | 128/2.06 R |
| 4,008,714 | 2/1977 | Silva et al. | 35/8 A X |
| 4,033,336 | 7/1977 | Murawski et al. | 128/2 D X |
| 4,098,274 | 7/1978 | Ebling et al. | 128/DIG. 13 X |
| 4,117,605 | 10/1978 | Kurland et al. | 35/9 A |

OTHER PUBLICATIONS

Palley, N. A. et al., "Computerized System for Routine Cordiac Output Measurements," 23ACEMB, Wash. D. C. Nov. 15-19, 1970 pp. 8-31.
Shiozawa, K. et al., "ICU and CCU systems of Nihon-kohden" Japan Elect. Engr., Oct. 1970, No. 47, pp. 75-77.
Riggert H.R. "Electronic Monitoring of Hospital Patients," Hewlett-Packard Journal, Jun. 1967, pp. 1-12.
Wallace, R. A., "Instrumentation for a Wearable Artificial Kidney," Med. & Biol. Engrg. & Computing, 1977, vol. 15, pp. 75-77.

Primary Examiner—Robert W. Michell
Assistant Examiner—Francis J. Jaworski
Attorney, Agent, or Firm—Tilton, Fallon, Lungmus & Chestnut

[57] ABSTRACT

A mechanism for aurally instructing a patient whose circulatory system is coupled to an infusion or exchanging machine and which includes a comparing means for discriminating between various malfunctions of the machine and reporting serially those of higher priority, with the objective of instituting a corrective feedback through specific directions to operator.

2 Claims, 3 Drawing Figures

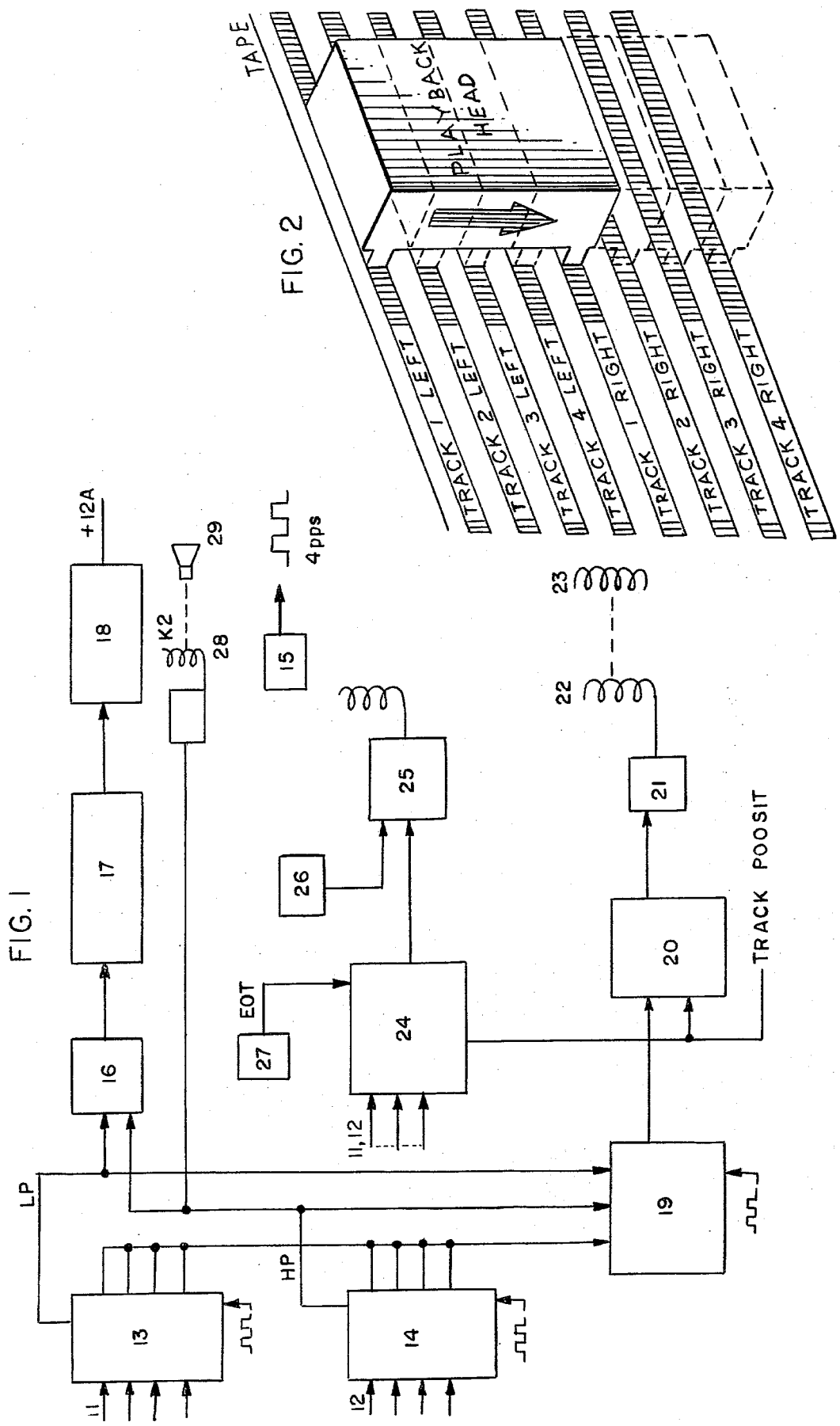

MECHANISM FOR AURALLY INSTRUCTING A PATIENT AND METHOD

BACKGROUND AND SUMMARY OF INVENTION

This invention relates to mechanism for aurally alerting and instructing a patient and, more particularly, to a patient whose circulatory system is coupled to a machine such as a machine for performing infusion, dialysis, etc. When such machines malfunction, there can be a threat to the patient's life and therefore it is most important that the malfunction be remedied immediately. Increasingly, such machines are being used by patients in their own homes so it is necessary for the patient to undertake the remedy. Inasmuch as the machinery is complicated and the parts interrelated, it is not unusual for a number of defects or malfunctions to occur simultaneously. To correct these on an organized fashion, and to reassure the patient while the correction is being undertaken, the invention provides a unique mechanism whereby the simultaneous malfunctions are prioritized and aural alerts and instructions are given to the patient on a priority basis.

Other objects and advantages of the invention may be seen in the details of construction and operation as set forth in the ensuing specification.

DETAILED DESCRIPTION

Figure 3:
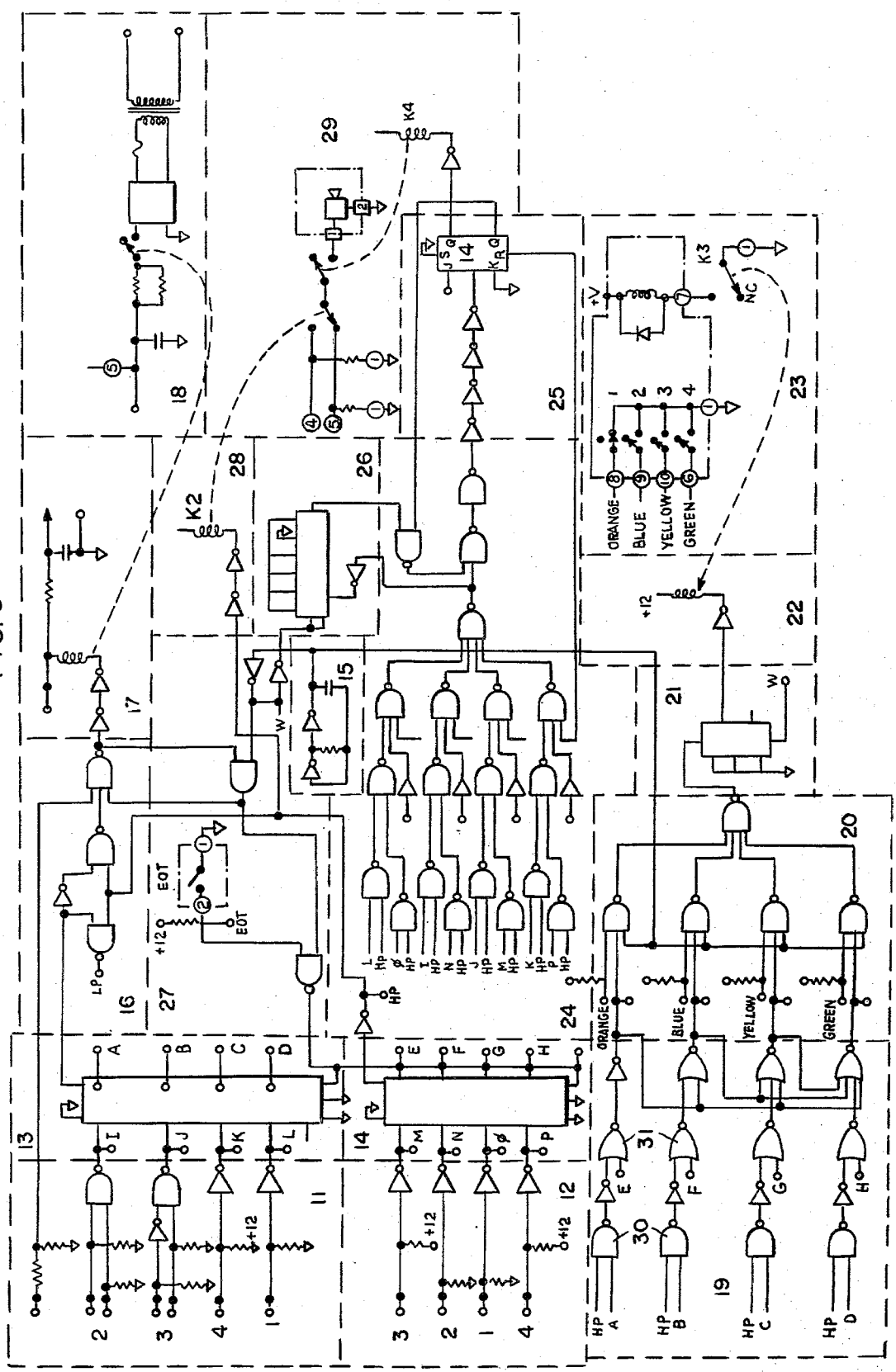

The invention is described in conjunction with an illustrative embodiment in the accompanying drawing, in which FIG. 1 is a block diagram illustrating the functional relationships of the various portions of the mechanism;

FIG. 2 is a fragmentary perspective view essentially schematic, of the playback head and tape employed in the practice of the invention; and FIG. 3 is a schematic diagram of the various circuits employed in one preferred embodiment which is illustrative of the invention and which corresponds, essentially (but in more detail) to the showing in FIG. 1.

The invention is first described in conjunction with one illustrative embodiment (with refererence to FIG. 1) and wherein the numeral 11 represents four signal inputs from a machine adapted to be coupled to a patient's circulatory system such as a kidney dialysis machine. The numeral 12, still referring to FIG. 1, represents another group of four signal inputs and, in the illustration given, the inputs 12 are of higher priority, i.e., greater criticality, than the inputs 11. The inputs 11 are delivered to an integrated circuit 13 while the inputs 12 are coupled to another integrated circuit 14. The circuits 13 and 14 sample the input lines in sequence to look for the presence of alarms. If none are present, the search, viz., sampling, continues at the rate of the oscillator 15 which oscillates at the rate of four pulses per second. When one or more alarms are detected, outputs are fed to the turn-on power circuit 16 which activates a 12-volt DC power supply via circuits 17 and 18.

The number 19 designates a comparing circuit which receives outputs from integrated circuits 13 and 14 and which are compared with the high priority signal HP from circuit 14. The numeral 20 designates a comparator which receives track position information from the tape deck to achieve a lock on to the proper track corresponding to the highest priority alarm which exists. The playback head is shown in the track 1 position in FIG. 2 and the three dotted configurations show the positions for tracks 2, 3 and 4.

When circuit 19 pulses the lock-on comparator 20, a signal is developed through a flip-flop circuit 21 to cycle a track advance relay 22 resulting in advance of the reply heads in a 1 to 2 to 3 to 4 to 1 sequence by the track advance solenoid 23 until proper coincidence is indicated by the track position signal. Thus, the circuits 19-23 operate as selector means to select the track of the tape carrying repair information corresponding to the severest fault sensed.

The circuit 24 relates the inputs from the eight alarms and the high and low priority signals to turn on the audio through a sound flip-flop circuit 25 during periods of alarm and also prevents messages from starting except at the beginning as determined by the end-of-tape switch 27. A delay circuit 26 retards operation of the sound enable flip-flop circuit 25 so as to prevent undesired audio turn-off.

The numeral 28 designates the right/left channel relay and relates the high priority outputs from the integrated circuit 14 to select the left hand channel for these high priority messages which will be picked up from the tape-deck by relay 28 and converted to sound by the speaker 29.

A more detailed description of the aural alerting mechanism will now be given and with respect to FIG. 3. As much as possible, the wiring diagram and circuity of FIG. 3 is keyed by dotted line blocks to the block diagram schematic of FIG. 1. Thus, the numeral 11 occurring in the upper left hand corner designates the components which sense four low priority signals. The numeral 12 designates the four inputs of high priority. For a kidney dialysis unit, these can be prioritized as follows:

|      | Priority No. | Description of Sensor |
| ---- | ------------ | --------------------- |
| LOW  | 1            | Foam Detector         |
|      | 2            | Blood Leak Detector   |
|      | 3            | Arterial Pressure     |
|      | 4            | Venous Pressure       |
| HIGH | 1            | Water Pressure        |
|      | 2            | Conductivity          |
|      | 3            | Temperature           |
|      | 4            | Dialysate Pressure    |

A typical scenario resulting from a signal delivered, for example by the temperature sensor, may be the following:

"Please push the Alarm Silence Button, Mr. Jones, and play close attention. The high temperature alarm that you are experiencing can be due to several things. First, look to see if you have accidentally moved the temperature knob. If you have not, turn the knob to increase the temperature. Remember that you have tempered water at your house. Feel the in-coming water line to see if the water might be too hot."

To achieve this type of aural instruction which also is ordered or prioritized, the signals going to the integrated circuits 13 and 14 are conditioned to a common polarity for input and then delivered to the Up counter circuits contained in the integrated circuits 13 and 14.

Necessarily, all of the connections cannot be seen—particularly those coming from the clock or oscillator 15. Again all of the interconnections are not shown but the circuitry can be understood because of the use of letters and other designations. For example, the circuit 19 is seen again in the lower left hand portion of the diagram and includes inputs A, B, C, D corresponding to the outputs from the low priority integrated circuit 13. Each of the gates 30 receiving a specific low priority signal also receives a high priority information (HP) signal. Gates 31 in another group receive a signal from a given gate 30 and a specific high priority signal as at E, F, G and H. Manifestly, no actuation of the circuit 19 occurs unless the sampling of the integrated circuits 13 and 14 is interrupted by the presence of a signal indicating a malfunction. Once, however, a signal indicative of a malfunction is presented, the circuit 19 operates to select the proper channel on the four-track tape for giving an audio message to the patient or other listener.

As illustrated, the tape deck is set up with the head on track 1, viz., the orange coded terminal as can be appreciated from the arrangement of elements in the circuit block designated 23. Thus, if the signal comes either from output A or E representing low priority conductivity or high priority arterial pressure, the track advance relay 22 is not energized and the contacts K3 at the very extreme right remain in the normally closed position. Thus, the track advance solenoid is not actuated and the tape head remains in its given condition. However, if the signal is anything other than conductivity or arterial pressure, the circuit 20 compares the position of the playback head with that of the signal and through the flip-flop circuit 22 energizes the track advance relay 22 to achieve the proper head position.

Thus, the circuits 12–23 constitute a signal sensing and comparing means for (a) positioning the playback head on the right track and (b) for discriminating between high and low priority signals.

It will also be noted that the control circuit 24 receives inputs from the various detection terminals I through P and which are associated with signals from the opposite integrated circuit 13 or 14. There are also inputs from the track position terminals, viz., orange, blue, yellow, green. Thus, when the circuits 19—23 have positioned the playback head properly, the control circuit 17 delivers a signal via the flip-flop 25 to the relay K4 which energizes the speaker 29. At the end of the tape, the circuit 27 delivers a signal to the control circuit 24 shutting down the speaker 29 except if there is a signal from the delay circuit 26 to the flip-flop 25 and the playing of the tape until the malfunction is corrected.

Thus, the control circuit 24 in combination with the circuits 25-28 serve to provide the aural signal and continue the same until the fault is corrected. Moreover, the circuits 19-23 in combination with the circuits 24—28 provide a specific word signal for a given fault and continue the word signal instructions until the fault has been remedied—all the while discriminating between simultaneous signals for different faults to give correction instructions for the fault of greater severity, i.e., criticality.

While in the foregoing specification a detailed description of a preferred embodiment of the invention has been set down for the purpose of illustration, many variations in the details hereingiven may be made by those skilled in the art without departing from the spirit and scope of the invention.

I claim:

1. Mechanism for aurally instructing a patient as to a malfunction of a kidney dialysis machine connected to the patient's circulatory system, comprising: a kidney dialysis machine adapted to be connected to the patient's circulatory system, a plurality of sensor means operably associated with said machine and arranged to report malfunctions of a specific nature, said malfunctions being grouped into high priority items relating to the patient's blood and low priority items relating to the dialysate, selector means coupled to said sensor means to prioritize simultaneous reports from said sensor means and deliver an appropriate signal to audio means, and an audio means including a plurality of taped messages and speaker means selectively responsive to said signal from said selector means, said audio means also including a tape playback head capable of generating a signal reflecting tape playback head positioning, said selector means including a comparator for receiving a malfunction signal and a signal reflecting tape playback head positioning, comparing the same and delivering a signal to activate said playback head until a predetermined position is achieved whereby an unattended patient undergoing dialysis is given instructions for correcting said malfunctions.

2. A method for aurally instructing a patient as to a malfunction of a kidney dialysis machine connected to the patient's circulatory system comprising:

connecting a kidney dialysis machine to the patient's circulatory system,
  said machine having a plurality of sensor means and audio means associated therewith and arranged to report malfunctions of a specific nature, said audio means including a plurality of taped messages and speaker means selectively responsive to said selector means,
grouping said malfunctions into high priority items relating to the patient's blood and low priority items relating to the dialysate, receiving specific malfunction reports from said sensor means,
evaluating said reports in accordance with said priorities established in said grouping step, producing and delivering to said audio means, in response to said evaluating step, a signal representative of said prioritized malfunctions, and
energizing said audio means in response to said signal to aurally instruct said patient as to said specific malfunctions and actions to be taken to remedy the same.

* * * * *